United States Patent [19]

Fenster

[11] Patent Number: 5,107,836
[45] Date of Patent: Apr. 28, 1992

[54] BODY IMPLANTABLE ELECTRICAL SIGNAL GENERATOR WITH REDUNDANT LEAD RETAINER AND SURGICAL PROCEDURE

[76] Inventor: Harold A. Fenster, 152 Marina Bay Dr., New Smyrna Beach, Fla. 32169

[21] Appl. No.: 592,249

[22] Filed: Oct. 3, 1990

[51] Int. Cl.[5] .............................................. A61N 1/362
[52] U.S. Cl. ...................................................... 128/419
[58] Field of Search ..................................... 128/419 P

[56] References Cited

U.S. PATENT DOCUMENTS

| 3,598,128 | 8/1971 | Chardack | 128/419 P |
|---|---|---|---|
| 4,013,081 | 3/1977 | Kolenik | 128/419 P |
| 4,180,078 | 12/1979 | Anderson | 128/419 PG |

FOREIGN PATENT DOCUMENTS 2720062 11/1978 Fed. Rep. of Germany ... 128/419 P

*Primary Examiner*—William E. Kamm
*Assistant Examiner*—Scott M. Getzow
*Attorney, Agent, or Firm*—Antonelli, Terry, Stout & Kraus

[57] ABSTRACT

A body implantable electrical signal generator (100) having a signal generator (18) disposed in a housing (24) for generating an electrical signal which is coupled to a part of the body by at least one electrical lead (16) connected between the signal generator and the part of the body in accordance with the invention that includes a plurality of lead retainer (30) disposed at spaced apart locations with respect to an outside surface of the housing upon implantation into the body but are individually movable with respect to the housing during the surgical procedure, the lead retainers being formed from a flexible material which yields when a portion of the electrical lead is forced into the lead retainer to capture the electrical lead, but after yielding, retains the electrical lead within the retainer so that the electrical lead is not free to move with respect to the retainer after the electrical signal generator is implanted in the body.

30 Claims, 3 Drawing Sheets

BODY IMPLANTABLE ELECTRICAL SIGNAL GENERATOR WITH REDUNDANT LEAD RETAINER AND SURGICAL PROCEDURE

TECHNICAL FIELD

The present invention relates to body implantable electrical signal generators and surgical procedures for implanting body implantable electrical signal generators.

BACKGROUND ART

Medical procedures have been developed in which body implantable electrical signal generators are implanted in the body which generate electrical signals for stimulating parts of the body with the electrical signal generated by the signal generator. The most common type of body implantable electrical signal generator is the heart pacemaker. Procedures are well developed for implanting heart pacemakers. Additionally, other implantable electrical signal generators exist such as defibrillators and nerve stimulators which generate electrical signals for application to the heart and the nerves respectively.

FIGS. 1 and 2 illustrate a prior art heart pacemaker 10 which has been implanted in the body 12 of a person by an incision 14. An electrical lead 16 couples an electrical signal generated by signal generator 18 to the heart 20. The electrical lead 16 is connected to a connector assembly 22 which completes an electrical connection to the signal generator 18 retained within housing 24. The incision 14 is typically made on the anterior superior chest wall 3 to 4 centimeters inferior to the mid-portion of the clavicle and cut to the level of the pectoral fascia. A pocket is formed within the patient's body for retaining the pacemaker 10. The electrical lead 16 is introduced into the subclavian vein 26 or cephalic vein and hence into the subclavian vein and forwarded down into the right ventricle of the heart 20 where the end thereof is attached to the ventricle to receive the electrical signal generated by the signal generator.

FIG. 1 illustrates an undesirable implantation of a pacemaker 10 in that the electrical lead 16 is too long for the distance between the connector 22 and the right clavicle. The portion 27 of the electrical lead 16 is redundant. Redundant lead wire 27 produces a bulge which can occur anywhere in the redundant lead. When the redundant lead wire 27 is wrapped around the periphery of the pacemaker, perpendicular to the thickness of the pacemaker (which is the desired positioning of redundant lead wire in a surgical procedure for implanting a pacemaker), bulging can load the redundant lead wire which applies a force to the lead along its longitudinal axis. As a result of the relative stiffness of the electrical lead 16, this force can potentially be transmitted to the ventricular wall of the heart with the possibility of perforation of the ventricular wall where the tip of the electrical lead 16 is attached to the ventricular wall. Loading in the other direction can cause bulging of the lead in or near the pocket resulting in patient discomfort.

FIG. 2 illustrates the optimal prior art procedure for implanting of a pacemaker. However, it should be understood that the connector is typically rotated 90° counterclockwise and the housing 24 is rotated 180°. With respect to FIG. 2, the redundant electrical lead wire 27 is wrapped by hand around the heart pacemaker 10 by the surgeon to create one or more coils 29. The pacemaker 10 is then introduced into the pocket. As a consequence of the physical size of patients varying substantially and pacemakers coming with only standard lengths of the electrical lead 16, the surgeon is faced with the task of coiling one or more coils 29 around the periphery of the pacemaker 10 in a direction perpendicular to the thickness of the unit. These coils 29 must be held in place by the surgeon's fingers and introduced into the pocket formed underneath the incision 14. This procedure requires delicate manipulations of the surgeon's fingers The prior art, as illustrated in FIGS. 1 and 2, has a number of disadvantages. In the first place, when redundant electrical lead 27 is present, buckling of the lead may occur which also can cause undue loading in a portion of the lead 16 which could cause breakage or couple force to the right ventricle as described above. Additionally, the redundant lead 27 may interfere with sensing by the generator. Furthermore, the wrapping of the lead around the periphery of the housing 24 is a cumbersome and potentially time consuming process. The insertion of the lead wrapped around the periphery of the housing 24, as illustrated in FIG. 2, can be difficult. If the one or more coils 29 fall away from the periphery of the housing during placement within the pocket, it is necessary for the surgeon to rewrap the coils. As a result, additional time can be required in completing the surgical procedure of implanting the pacemaker with the attendant increase in costs consequent from payment of operating room and hospitalization fees. Redundant lead wire 27 positioned under the generator against the chest wall can decrease sensing sensitivity by electrical interference. Redundant lead wire 27 positioned above the generator and below the skin can interfere with the conventional generator programming which is performed in and out of the operating room by causing undesirable electrical interference. Finally, since the implanting of a pacemaker is not done under general anesthesia, prolonged operating time required for positioning the coiled redundant wire in place into the subcutaneous pocket can result in additional discomfort to the patient.

The prior art, as illustrated in FIGS. 1 and 2, does not provide any mechanism for retaining redundant lead 27 on the pacemaker in a fixed position to facilitate the elimination of redundant lead. Even if the surgeon is able to coil the electrical lead around the periphery of the generator housing 24 to eliminate the redundant lead 27 of FIG. 1, the likelihood is that the surgical procedure was complicated by requiring delicate and time-consuming manipulations of the redundant wire in coiling it around the periphery of the pacemaker.

German Offenlegungsschrift 27 20 662 discloses a pacemaker system which attaches redundant lead to the body of the pacemaker with a continuous or spaced apart clamps which permit attachment of redundant lead around the periphery of the pacemaker perpendicular to a thickness of the housing of the pacemaker. However, the continuous or spaced apart clamps have the disadvantage of being fixed to the housing of the pacemaker and not easily shifted with respect to the housing during the surgical procedure which prevents the surgeon at the time of positioning the redundant lead in the clamps from easily shifting the position of the clamps with respect to the housing. The inability to easily shift the position of the clamps during surgery makes it more difficult for the surgeon to deftly manipulate the clamps with respect to the housing to eliminate bulges especially at a point at which the electrical lead is attached to the pacemaker or the point where the electrical lead enters the subclavian vein to avoid the potential transmission of force to the ventricular wall. As a result, the disclosed system could be difficult to use in taking up redundant lead during a surgical procedure and the inventor is not aware of this device being commercialized.

U.S. Pat. No. 3,598,124 discloses a lead storage for a pacemaker in which the electrical lead is free to be released as a consequence of the signal generator being free to rotate to play out additional lead as the patient grows which is a common problem for pediatric pacemakers. The pacemaker of the '124 patent does not retain the lead in a fixed position around the periphery of the housing in accordance with the desired procedure as illustrated in FIG. 2. The '124 patent teaches that redundant lead is "an unsatisfactory situation where the extra lead lies within the body". Moreover, the '124 patent teaches that "normal movement of the body may cause problems with the loose extra lead length causing it to, for example, undesirably entwine itself around a portion of the body".

U.S. Pat. No. 4,013,081 discloses a pediatric cardiac pacemaker in which extra electrical lead is coiled and retained within a bag such that, as the patient grows, a large spiral path around the pacemaker can tighten to a smaller spiral to accommodate the greater distance between the heart and the pacemaker as the patient grows. The '081 patent does not retain the lead in a fixed position with respect to the periphery of the pacemaker.

It is estimated that the vast majority of pacemakers which are implanted currently use fixed length leads for patients who are fully grown.

DISCLOSURE OF INVENTION

The present invention is an improved body implantable electrical signal generator and surgical procedure for implanting a body implantable electrical signal generator. The invention facilitates the surgeon's eliminating loose, redundant electrical lead coupling a signal generator to a part of the body being stimulated by the electrical signal. As a result, the problems associated with the prior art are eliminated in that the present invention retains any redundant electrical lead in a plurality of lead retainers which may be easily individually shifted relative to the electrical signal generator during the surgical procedure. This facilitates the elimination of the redundant electrical lead wire. Upon completion of the surgical procedure, the retainers will be fixed at spaced apart locations which will not move with respect to an outside surface of the housing of the electrical signal generator. The lead retainers are formed from a flexible material which yields when a portion of the lead is forced into the lead retainer by a surgeon to capture the lead. After yielding, the retainers retain the lead within the retainer so that the lead is not free to move with respect to the retainer after the electrical signal generator is implanted by the surgeon in the body. The retainers are formed from a material which is inert in the body and inexpensive.

With the invention, the problem of coiling the redundant electrical lead connecting the electrical signal generator to the part of the body being stimulated, as illustrated in FIG. 2, is eliminated. The surgeon positions the individual lead retainers relative to the housing to provide optimum take-up of redundant lead and forces any excess redundant electrical lead into the retainers at the spaced apart locations so that the redundant electrical lead is no longer free to move prior to positioning the electrical signal generator in a pocket formed within the patient's body. The coils of electrical lead, as illustrated in the prior art of FIG. 2, are not free to move away from the periphery of the electrical signal generator. Delicate manipulations of the hands to keep the coiled redundant lead positioned around the periphery of the electrical signal generator are no longer necessary as a result of the retainer freeing the surgeon's fingers from having to hold the coils of the electrical lead against the periphery of the electrical signal generator as the electrical signal generator is inserted into the subcutaneous pocket in which the electrical signal generator is retained in the body. The operating room time required to implant the electrical signal generator is reduced, discomfort to the patient is reduced as a consequence of requiring less operating time under local anesthesia and the time required for the surgeon to complete the surgical procedure is reduced. Reducing of the time required to implant a electrical signal generator has cost benefits in that charges for operating room time and the time required by the surgeon to complete the procedure are reduced.

A body implantable electrical signal generator having a signal generator disposed in a housing for generating an electrical signal which is coupled to a part of the body by at least one electrical lead connected between the signal generator and the part of the body in accordance with the invention that includes a plurality of lead retainers mounted at spaced apart locations with respect to an outside surface of the housing upon implantation into the body but are individually movable with respect to the housing during the surgical procedure, the lead retainers being formed from a flexible material which yields when a portion of the electrical lead is forced into the lead retainer by a surgeon to capture the electrical lead but after yielding retains the lead within the retainer so that the electrical lead is not free to move with respect to the retainer after the electrical signal generator is implanted by the surgeon in the body. At least one of the lead retainers comprises a channel formed from the flexible material with an opening extending along the channel and facing outward from the outside surface of the housing to split the channel into two parts which are separated by a distance less than an outside diameter of the electrical lead, the force causing the parts to separate by a distance at least as great as a diameter of the electrical lead and causing the electrical lead to be retained within the channel. A periphery of the housing is perpendicular to a thickness of the housing and the lead retainers are disposed at spaced apart locations along the periphery. The lead retainers are formed from a material which is inert in the body. The lead retainers can retain a plurality of different sections of the electrical lead to permit multiple turns of a single lead to be attached to the housing or a plurality of electrical leads to be attached to the housing. Preferably, the lead retainers comprise a plurality of channels with each of the channels formed from the flexible material and preferably disposed tangential to the periphery.

The lead retainers may be attached to at least one stretchable band, each band being attached to the outside surface of the housing by a tension in the band retaining the band in surface contact with the housing generated by deformation of the band. The relative position of each lead retainer may be moved relative to the housing during the surgical procedure as a result of the elasticity of the band permitting shifting of the point of engagement of the band with the periphery without shifting a diametrically opposite point of engagement of the band with its point of engagement to the housing. The electrical signal generator may be a heart pacemaker, defibrillator or nerve stimulator but is not limited thereto.

A surgical procedure for implanting a body implantable electrical signal generator having a signal generator disposed in a housing for generating an electrical signal which is coupled to a part of the body by at least one electrical lead connected between the signal generator and the part of the body and a plurality of lead retainers mounted at spaced apart locations with respect to an outside surface of the housing upon implantation into the body but are individually movable with respect to the housing during the surgical procedure and being formed from a flexible material which yields when a portion of the electrical lead is forced into the lead retainer by a surgeon to capture the electrical lead, but after yielding, retains the electrical lead within the lead retainer so that the lead is not free to move with respect to the retainer after the electrical signal generator is implanted by the surgeon in the body in accordance with the invention includes making an incision in the body and forming a pocket in the body to retain the body implantable electrical signal generator; attaching the electrical lead to the part of the body which is to be stimulated; and retaining any redundant electrical lead, which is a length of lead greater than a desired length of electrical lead connecting the signal generator to the part of the body, in the lead retainers after the lead retainers are individually positioned with respect to the housing during the surgical procedure by wrapping the electrical lead around the housing and forcing the excess electrical lead into the lead retainers so that only the electrical lead necessary to connect the signal generator to the part of the body is free to move after the incision is closed.

BEST MODE FOR CARRYING OUT THE INVENTION

Figure 2:
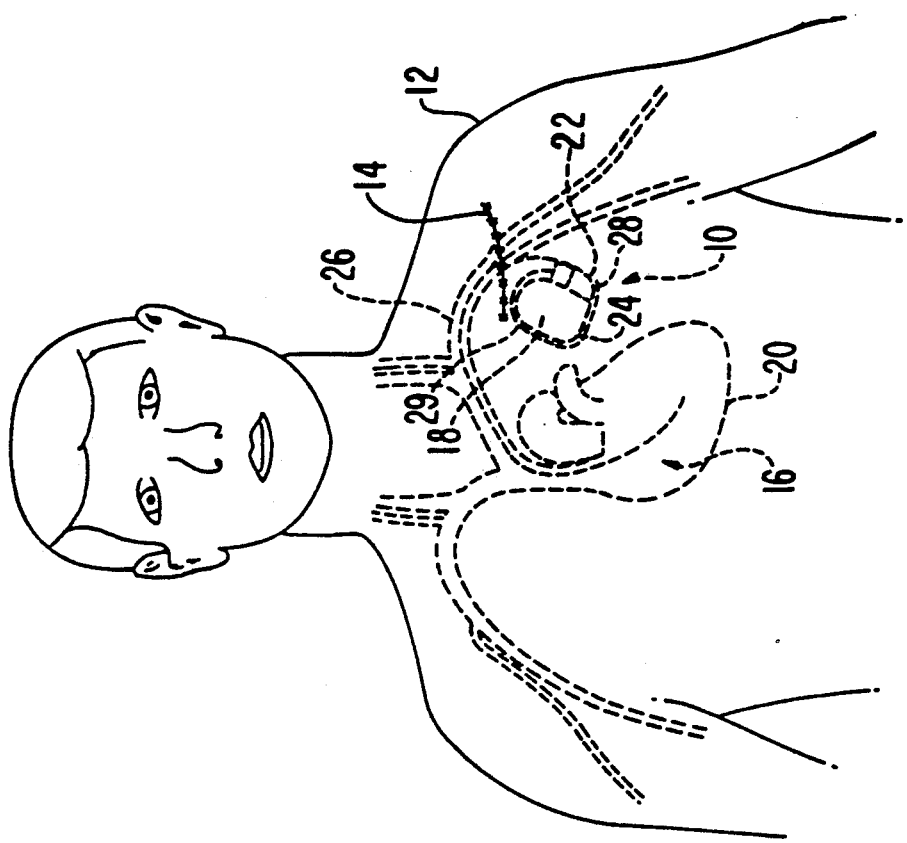
FIGS. 1 and 2 illustrate a prior art implantation of a pacemaker.
Figure 1:
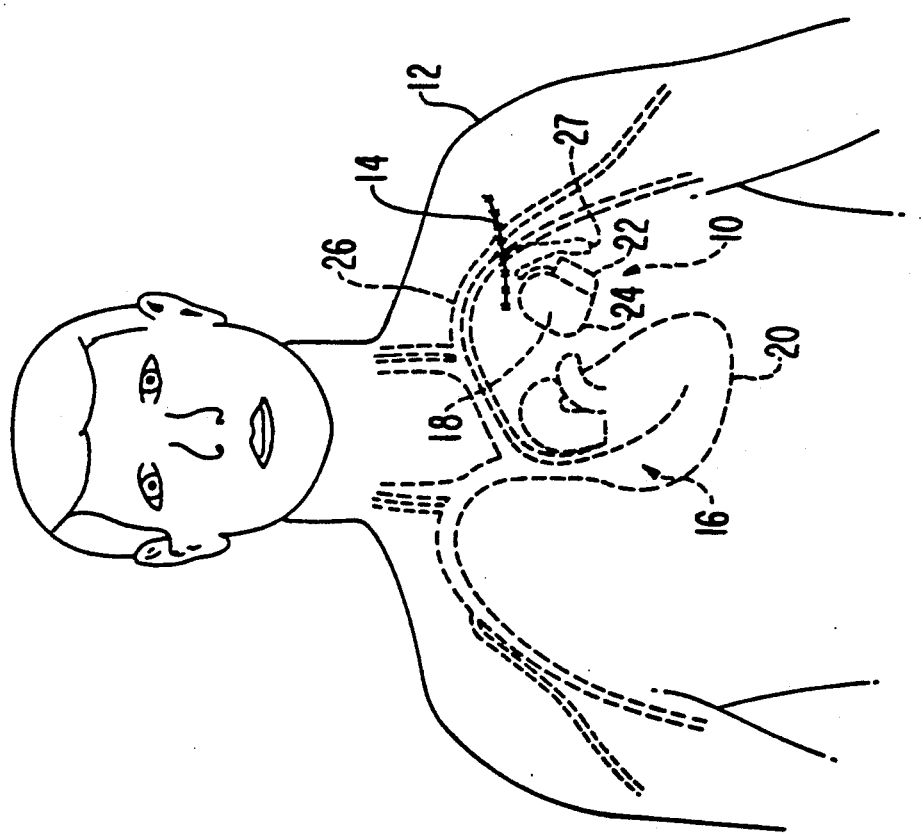
Figure 3:
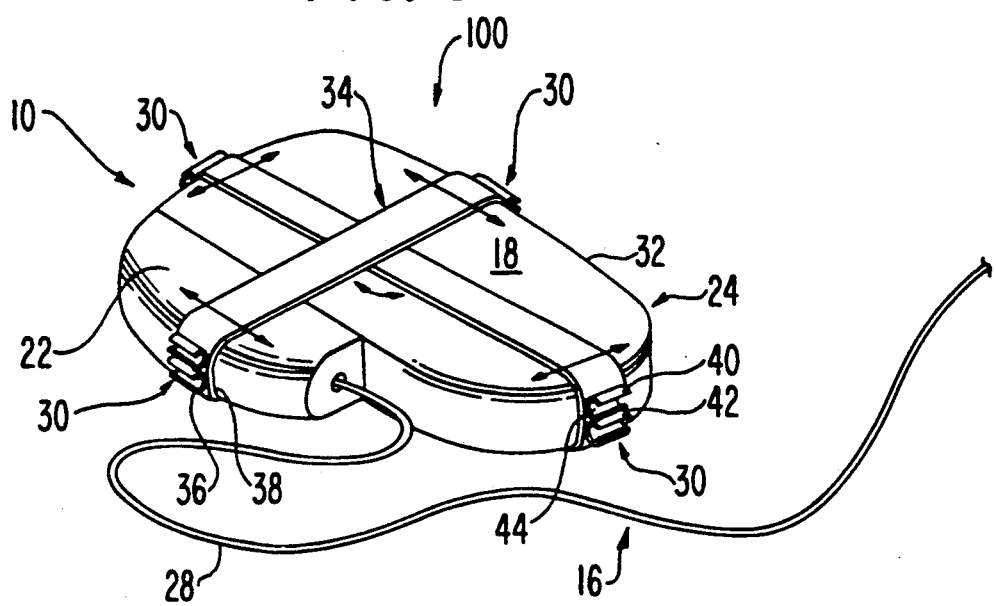
FIG. 3 illustrates a first embodiment of a body implantable electrical signal generator in accordance with the present invention.
Figure 4:
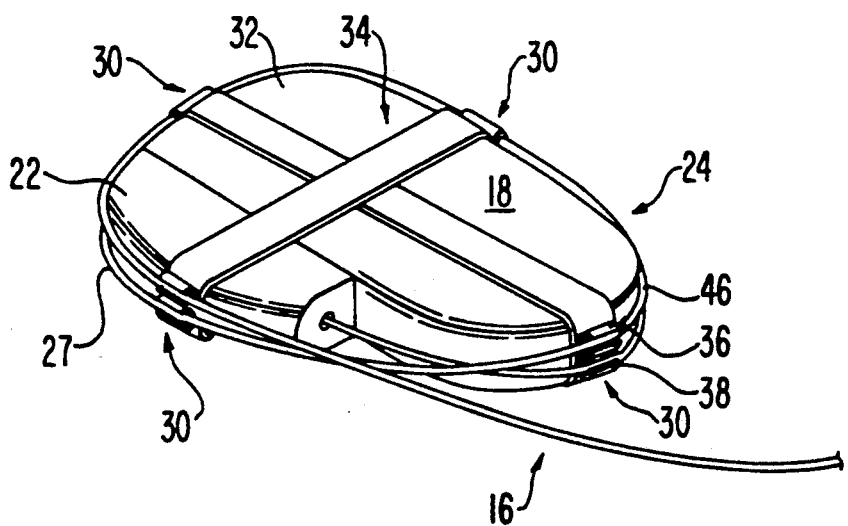
FIG. 4 illustrates the retaining of an electrical lead by the embodiment of FIG. 3.
Figure 5:
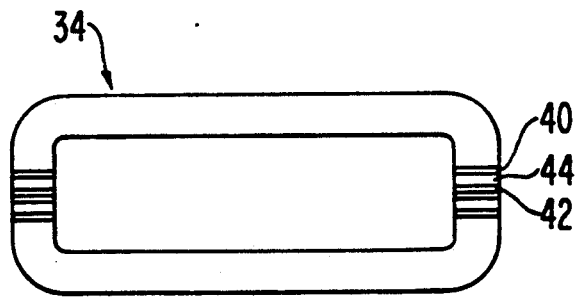
FIG. 5 illustrates a band utilized with the embodiment of FIG. 3.

FIGS. 3-5 illustrate a first embodiment 100 of a body implantable electrical signal generator in accordance with the present invention. Like reference numerals identify like parts in FIGS. 1-3. The body implantable electrical signal generator, which may be but is not limited to being a pacemaker, defibrillator or nerve stimulator signal generator may be of any conventional design. The electrical lead 16 is in accordance with the prior art which is available in standard lengths which result in redundant lead 27 as discussed above with reference to FIG. 1 when the electrical signal generator is implanted in patients of different physical size. At least one electrical lead is connected between the connector 22 and the part of the body to be stimulated. A plurality of lead retainers 30 are disposed at spaced apart locations with respect to an outside surface 32 of the housing 24. The lead retainers 30 are formed from a flexible material which may be a polymeric silicon substance having the properties of rubber which is biologically inert and used in surgical prosthesis such as Silastic TM. As illustrated, the lead retainers 30 are attached to bands 34 as illustrated in FIG. 5. Preferably, a pair of bands 34 are attached respectively to the outside surface 32 of the housing 24 along major and minor axes of the housing which respectively span the length and width. The bands 34 are stretchable. The stretchable bands 34 permit the surgeon to individually position each lead retainer 30 with respect to the outside surface of the housing. The relative angle subtended between the bands 34, as indicated by the curved two headed arrow, may be varied to move the relative position of the lead retainers 30 from the 90° orientation as illustrated during the surgical procedure. For example, without limitation the relative angle may be 45° by shifting one band with respect to the housing by stretching the band and rotating it relative to the housing 24. Furthermore, each individual lead retainer 30 may be shifted relative to the housing as a consequence of the elasticity of the bands 34 during the surgical procedure. The ability to move the individual lead retainers 30 during the surgical procedure, as indicated by the straight two headed arrows of FIG. 3, permits optimization of taking up redundant lead wire 28 without difficult hand manipulations on the part of the surgeon which facilitates the elimination of the redundant lead wire and bulges in the redundant lead. After final positioning, each band 34 is attached to the outside surface 32 of the housing 24 by tension in the band which retains the band in surface contact with the outside surface 32 of the housing 24 generated by deformation of the band which preferably is elastic deformation. The crossing of the bands also prevents relative movement of the bands after they are finally positioned by the surgeon. The bands 34 also are formed from the aforementioned polymeric silicon or other acceptable body implantable material having the property of rubber which is biologically inert and used in surgical prosthesis. Each of the lead retainers 30 preferably has a plurality of channels 36 having an opening extending along the channel and disposed outward from the outside surface 32 of the housing 24 to split the channel into two parts 40 and 42 which are separated by a distance 44 which is less than an outside diameter of the electrical lead 16. During the surgical procedure in which the body implantable electrical signal generator is implanted into the body, the surgeon forces any redundant lead wire 27 of the at least one electrical lead 16 into the space 44 between the parts 40 and 42 which causes the parts to separate by a distance at least as great as a diameter of the electrical lead and causes the electrical lead to be retained within the channel as illustrated in FIG. 4. The redundant lead wire 27 is retained in one or more coils 46 along the periphery of the housing 24 by retention in the same or different channels 36 and 38 which eliminates the possibility of the coils of the redundant lead wire coming loose either during the surgical procedure or after the surgical procedure for implanting the implantable electrical signal generator has been completed with the attendant problem discussed above with respect to the prior art.

Figure 6:
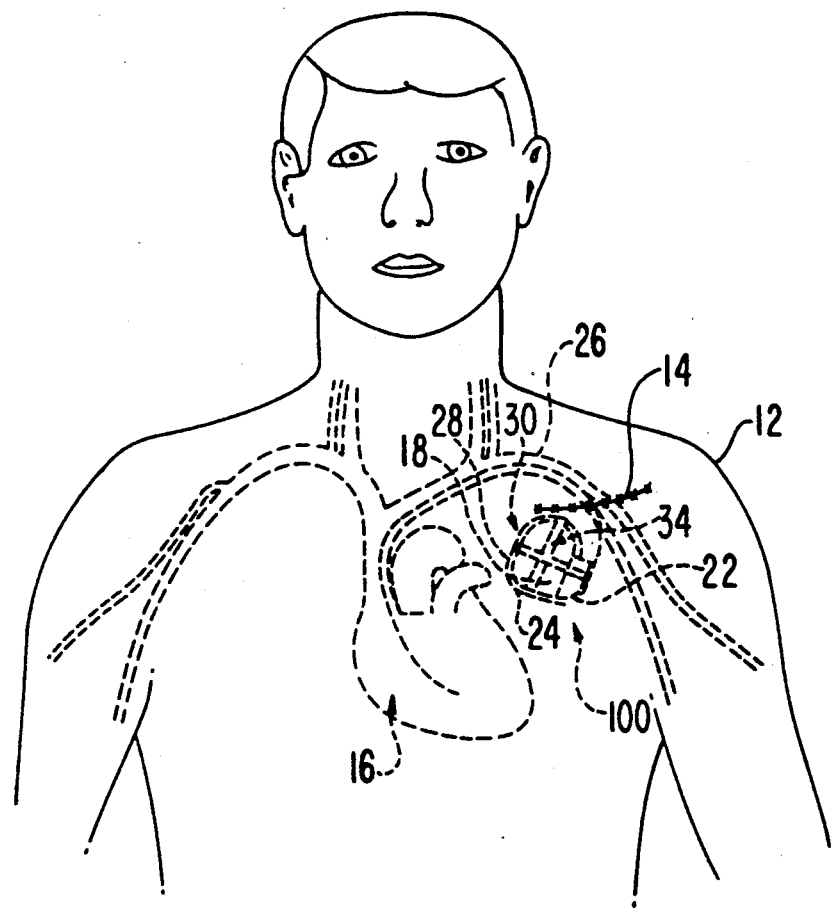
FIG. 6 illustrates a surgical procedure in accordance with the present invention.

FIG. 6 illustrates a surgical procedure in accordance with the present invention. As illustrated, the procedure illustrates the embodiment 100 of FIGS. 3-5 but it should be understood that the surgical procedure is not limited thereto. Like reference numerals identify like parts in FIGS. 1-8. The incision 14 is made in the body 12. A pocket is formed in the body to retain the body implantable electrical signal generator 100 in accordance with conventional practice. The lead wire 16 is attached to the part of the body which is to be stimulated which, as illustrated in FIG. 6, is the right ventricle of the heart. Any redundant lead wire 27, which is a length of lead greater than a length of lead wire necessary to connect the signal generator 18 to the part of the body, is retained in lead retainers 30 where it is retained by the channel 36 by the parts 40 and 42 pressing against an outside surface of the redundant wire 28 by wrapping the lead around the housing 24 and forcing the redundant lead 28 into the lead retainers 30 so that only the lead necessary to connect the signal generator to the part of the body is free to move after the incision is closed. The spacing between the individual lead retainers 30 is varied by stretching of the elastic bands 34 to position the individual lead retainers relative to the housing 24 for providing a desired final position if the lead retainers relative to the housing after the surgical procedure is complete. The angle between the bands or the position of the individual lead retainers may be varied as indicated by the bidirectional arrows in FIG. 3.

While the invention has been described in terms of its preferred embodiments and a method of surgical procedure, it should be understood that numerous modifications may be made thereto without departing from the spirit and scope of the present invention. While preferred applications of the present invention are for body implantable pacemakers, defibrillators and nerve electrical signal generators, it should be understood that the present invention may be utilized in any applications involving body implantable devices in which excess electrical lead is to be retained in a fixed position with respect to the implantable device. It is intended that all such modifications fall within the scope of the appended claims.

I claim:

1. A body implantable electrical signal generator having a signal generator disposed in a housing for generating an electrical signal which is coupled to a part of the body by at least one electrical lead connected between the signal generator and the part of the body comprising:

a plurality of lead retainers disposed at spaced apart locations with respect to an outside surface of the housing upon implantation into the body but are individually movable with respect to the housing during the surgical procedure, the lead retainers being formed from a flexible material which yields when a portion of the lead is forced into the lead retainer to capture the lead, but after yielding, retains the lead within the retainer so that the lead is not free to move with respect to the retainer after the electrical signal generator is implanted in the body.

2. A body implantable electrical signal generator in accordance with claim 1 wherein at least one of the lead retainers comprises:

a channel formed from the flexible material with an opening extending along the channel and disposed outward from the outside surface of the housing to split the channel into two parts which are separated by a distance less than an outside diameter of the electrical lead, the force causing the parts to separate by a distance at least as great as a diameter of the electrical lead and causing the electrical lead to be retained within the channel.

3. A body implantable electrical signal generator in accordance with claim 2 wherein:

a periphery of the housing is perpendicular to a thickness of the housing and the lead retainers are disposed at spaced apart locations along the periphery.

4. A body implantable electrical signal generator in accordance with claim 3 wherein:

the lead retainers are formed from a material which is inert in the body.

5. A body implantable electrical signal generator in accordance with claim 4 wherein:

the lead retainers are attached to at least one stretchable band, each band being fixed to the outside surface of the housing by a tension in the band retaining the band in surface contact with the housing generated by deformation of the band.

6. A body implantable electrical signal generator in accordance with claim 3 wherein:

the lead retainers are attached to at least one stretchable band, each band being fixed to the outside surface of the housing by a tension in the band retaining the band in surface contact with the housing generated by deformation of the band.

7. A body implantable electrical signal generator in accordance with claim 2 wherein:

the lead retainers are formed from a material which is inert in the body.

8. A body implantable electrical signal generator in accordance with claim 7 wherein:

the lead retainers are attached to at least one stretchable band, each band being fixed to the outside surface of the housing by a tension in the band retaining the band in surface contact with the housing generated by deformation of the band.

9. A body implantable electrical signal generator in accordance with claim 2 wherein:

the lead retainers are attached to at least one stretchable band, each band being fixed to the outside surface of the housing by a tension in the band retaining the band in surface contact with the housing generated by deformation of the band.

10. A body implantable electrical signal generator in accordance with claim 1 wherein:

a periphery of the housing is perpendicular to a thickness of the housing and the lead retainers are disposed at spaced apart locations along the periphery.

11. A body implantable electrical signal generator in accordance with claim 10 wherein:

the lead retainers are formed from a material which is inert in the body.

12. A body implantable electrical signal generator in accordance with claim 11 wherein:

the lead retainers are attached to at least one stretchable band, each band being fixed to the outside surface of the housing by a tension in the band retaining the band in surface contact with the housing generated by deformation of the band.

13. A body implantable electrical signal generator in accordance with claim 10 wherein at least one of the lead retainers comprises:
  a plurality of channels, disposed tangential to the periphery, a plurality of the channels being formed from the flexible material with an opening extending along the channels and facing outward from the outside surface of the housing to split the channels into two parts which are separated by a distance less than an outside diameter of the electrical lead, the force causing the parts to separate by a distance at least as great as a diameter of the electrical lead and causing the electrical lead to be retained within the channels.

14. A body implantable electrical signal generator in accordance with claim 13 wherein:
  the lead retainers are formed from a material which is inert in the body.

15. A body implantable electrical signal generator in accordance with claim 14 wherein:
  the lead retainers are attached to at least one stretchable band, each band being fixed to the outside surface of the housing by a tension in the band retaining the band in surface contact with the housing generated by deformation of the band.

16. A body implantable electrical signal generator in accordance with claim 13 wherein:
  the lead retainers are attached to at least one stretchable band, each band being fixed to the outside surface of the housing by a tension in the band retaining the band in surface contact with the housing generated by deformation of the band.

17. A body implantable electrical signal generator in accordance with claim 10 wherein:
  the lead retainers are attached to at least one stretchable band, each band being fixed to the outside surface of the housing by a tension in the band retaining the band in surface contact with the housing generated by deformation of the band.

18. A body implantable electrical signal generator in accordance with claim 1 wherein:
  the lead retainers are formed from a material which is inert in the body.

19. A body implantable electrical signal generator in accordance with claim 18 wherein:
  the lead retainers are attached to at least one stretchable band, each band being fixed to the outside surface of the housing by a tension in the band retaining the band in surface contact with the housing generated by deformation of the band.

20. A body implantable electrical signal generator in accordance with claim 1 wherein:
  at least one of the lead retainers can retain a plurality of different sections of the at least one electrical lead.

21. A body implantable electrical signal generator in accordance with claim 20 wherein:
  the lead retainers are attached to at least one stretchable band, each band being fixed to the outside surface of the housing by a tension in the band retaining the band in surface contact with the housing generated by deformation of the band.

22. A body implantable electrical signal generator in accordance with claim 1 wherein at least one of the lead retainers comprises:
  a plurality of channels, a plurality of the channels being formed from the flexible material with an opening extending along the channels and facing outward from the outside surface of the housing to split the channels into two parts which are separated by a distance less than an outside diameter of the electrical lead, the force causing the parts to separate by a distance at least as great as a diameter of the electrical lead and causing the electrical lead to be retained within the channel.

23. A body implantable electrical signal generator in accordance with claim 22 wherein:
  the lead retainers are formed from a material which is inert in the body.

24. A body implantable electrical signal generator in accordance with claim 23 wherein:
  the lead retainers are attached to at least one stretchable band, each band being fixed to the outside surface of the housing by a tension in the band retaining the band in surface contact with the housing generated by deformation of the band.

25. A body implantable electrical signal generator in accordance with claim 22 wherein:
  the lead retainers are attached to at least one stretchable band, each band being fixed to the outside surface of the housing by a tension in the band retaining the band in surface contact with the housing generated by deformation of the band.

26. A body implantable electrical signal generator in accordance with claim 1 wherein:
  the lead retainers are attached to at least one stretchable band, each band being fixed to the outside surface of the housing by a tension in the band retaining the band in surface contact with the housing generated by deformation of the band.

27. A body implantable electrical signal generator in accordance with claim 1 wherein:
  the electrical signal generator is a heart pacemaker.

28. A body implantable electrical signal generator in accordance with claim 1 wherein:
  the electrical signal generator is a defibrillator.

29. A body implantable electrical signal generator in accordance with claim 1 wherein:
  the electrical signal generator is a nerve electrical signal generator.

30. A surgical procedure for implanting a body implantable electrical signal generator having a signal generator disposed in a housing for generating an electrical signal which is coupled to a part of the body by at least one electrical lead connected between the signal generator and the part of the body and a plurality of lead retainers fixed at spaced apart locations with respect to an outside surface of the housing upon implantation into the body but are individually movable with respect to the housing during the surgical procedure and being formed from a flexible material which yields when a portion of the electrical lead is forced into the lead retainer by a surgeon to capture the lead but after yielding retains the electrical lead within the retainer so that the electrical lead is not free to move with respect to the retainer after the electrical signal generator is implanted in the body comprising:
  making an incision in the body and forming a pocket in the body to retain the body implantable electrical signal generator;
  attaching the electrical lead to the part of the body which is to be stimulated; and
  retaining any redundant electrical lead, which is a length of electrical lead greater than a desired length of electrical lead connecting the signal generator to the part of the body, in the lead retainers after the lead retainers are individually positioned with respect to the housing during the surgical procedure by wrapping the electrical lead around the housing and forcing the redundant electrical lead into the lead retainers.

* * * * *